United States Patent
Placzek

[11] Patent Number: 5,119,994
[45] Date of Patent: Jun. 9, 1992

[54] METHOD AND APPARATUS FOR THE PROCESSING OF MEDICAL WASTE MATERIALS

[76] Inventor: Terrance M. Placzek, 31729 N. Cafe Line Rd., Tickfaw, La. 70466

[21] Appl. No.: 604,761

[22] Filed: Oct. 29, 1990

[51] Int. Cl.$^5$ .................................... B02C 19/12
[52] U.S. Cl. .............................. 241/17; 241/18; 241/21; 241/23; 241/26; 241/65; 241/284; 241/299; 241/606; 422/26; 422/33; 422/295; 422/309
[58] Field of Search .............. 422/26, 27, 32, 33, 422/104, 184, 203, 228, 229, 309, 295; 241/DIG. 14, DIG. 38, 23, 65, 66, 67, 299, 182, 183, 99, 17, 18, 57, 21, 284, 26; 366/227, 228

[56] References Cited
U.S. PATENT DOCUMENTS
4,974,781 12/1990 Placzek .................... 241/23 X FOREIGN PATENT DOCUMENTS
0128165 11/1978 Japan ................ 241/DIG. 38 X
0583562 11/1986 U.S.S.R. ............ 241/DIG. 38 X
1502093 8/1989 U.S.S.R. ............ 241/DIG. 38 X Primary Examiner—Mark Rosenbaum
Attorney, Agent, or Firm—Julian C. Renfro

[57] ABSTRACT

An apparatus and novel method for processing medical waste materials comprising an elongate pressure vessel of generally cylindrical configuration having an inlet end, and a closely fitting closure member for the inlet. An elongate drum of generally cylindrical configuration is mounted in the vessel for rotation about its longitudinal axis, which drum can be selectively driven in either rotative direction. The longitudinal axis of the drum is disposed at a slight angle of incline to the horizontal, placing the inlet end at a slightly higher elevation than the opposite end. A helically configured member is disposed along the interior perimeter of said drum, such that during rotation of the drum in a first rotative direction, the helically configured member moves the waste material in a direction away from the inlet end of the drum, whereas during rotation of the drum in the second rotative direction, the helically configured member moves the waste material toward the inlet. The helically configured member is utilized in conjunction with a plurality of non-obstructive lifting paddles that serve to effect a highly advantageous, very thorough mixing of the waste materials. Moisture and heat are typically utilized to aid the processing of the waste, such as by the addition of stem. Discharge of the fully processed waste material is effected when the drum is being rotated in the second rotative direction, after the closure member has been opened.

40 Claims, 4 Drawing Sheets

METHOD AND APPARATUS FOR THE PROCESSING OF MEDICAL WASTE MATERIALS

RELATION TO OTHER INVENTION

This invention bears a definite relationship to my allowed patent application Ser. No. 321,563, filed Mar. 9, 1989 and renamed "METHOD AND APPARATUS FOR PREPARING PAPER-CONTAINING AND PLASTIC-CONTAINING WASTE MATERIALS FOR COMPONENT FRACTION SEPARATING."- This application became U.S. Pat. No. 4,974,781, on Dec. 4, 1990.

BACKGROUND OF THE INVENTION

A rising consciousness concerning the proper handling and disposal of waste materials is occurring in people at every level of society. Among the most serious of the waste disposal problems is that of medical waste materials that potentially harbor infectious agents and diseases. Incidents of medical waste materials washing ashore along the coastlines and of bags of medical waste materials being dumped in ditches strike fear into the hearts of all people, causing an outcry for better controls.

Public opinion has caused a flurry of activity by legislators and regulators, particularly at the federal level, concerning the management of medical wastes. The Environmental Protection Agency (EPA), the Office of Technology Assessment (OTA), the Center for Disease Control (CDC) and the Occupational, Safety and Health Act (OSHA) have issued management guidelines and regulations regarding medical wastes including the Medical Waste Tracking Act.

Medical wastes that potentially harbor infectious agents have been identified by the OTA as being generated by hospitals, clinics, doctor's offices, dentist's offices, veterinarian's offices, mortuaries, laboratories and other medical and research facilities. Recognized options for handling and managing these wastes include incineration, microwaving, autoclaving, chemical treatment, hydropulping and land disposal. Nearly 80% of the hospital generators in this country use or have access to some type of combustion system to incinerate these wastes.

Combustion of medical wastes has the unfortunate effect of releasing pollutants into the air. Of primary concern is the release to the atmosphere, from the medical waste combustors, the pollutants of Hydrogen Chloride (HCl), Sulfur Dioxide ($SO_2$), particulate matter (PM), trace organics such as Dioxins and Furans, Arsenic (As), Cadmium (Cd), Chromium (Cr), Mercury (Hg), Lead (Pb), and others. Many of the combustion systems that are in service do not adequately control these pollutants and are a cause for concern. This concern has been addressed by Section III of the Clean Air Act (CAA), and these regulatory standards may preclude the use of medical waste combustion at many installations by requiring extensive control measure to be added to combustion facilities.

Medical waste generation rates have doubled in the past decade with a 50% increase occurring in the past three years alone. The increase is due to factors such as the increasing use of disposable materials and the redefinition of the regulated waste fraction. As diseases such as AIDS receive increasing public attention, increasing pressure will be brought to bear on the generators of medical waste to the extent that anything that comes into contact with a patient or a patient's blood or bodily fluids will be classified and managed as being potentially infectious. This circumstance is called "Universal Precautions" by the CDC.

With such circumstances developing, hospital administrators are forced to conduct a balancing act within their systems to minimize medical waste amounts that are potentially infectious and that are the most costly to manage, by having their staff segregate wastes in multiple containers within hospital rooms and operating rooms. This can lead to arbitrary decisions as to what is infectious and what is not, and places an additional burden upon a staff that often works under crisis conditions. The concern, of course, is that incorrectly classified material may be incorrectly disposed of. Incorrect disposal could result in violations of the regulations for management of these wastes with severe fines being levied on the violator or, in the worst case, be the cause of an outbreak of an infectious agent functioning to contaminate people. However, to practice no segregation of materials and to classify all waste as potentially infectious would be economically prohibitive to a generator.

In light of this growing dilemma, it has become highly appropriate to strive for the perfection of a method and an apparatus for the processing of medical wastes into ordinary, common wastes so that these wastes may then be managed for disposal or recycling in the commonly accepted general waste disposal system without the threat of the spread of an infectious agent.

SUMMARY OF THE INVENTION

The main objective of this invention is to provide a method and an apparatus that accomplishes the sterilization of medical waste materials while transforming the medical waste materials into ordinary, common waste materials having approximately ⅓ of their original volume, accomplished by the use of unique, bi-directional lifting paddles and directional flighting that are disposed in carefully located positions on the interior of an inclined, elongate drum rotationally disposed within a pressure vessel. These components effect a high degree of agitation of materials, facilitating the contacting of the materials with the sterilizing agent.

A major consideration of this invention is that the medical waste materials to be processed be handled and introduced into the apparatus without it being necessary beforehand to be size reduced, separated or removed from its protective Red Bag or container. The apparatus is therefore of sufficient size to accommodate the introduction and the subsequent processing of the medical waste materials in their Red Bags and containers.

The term "medical waste" in accordance with this invention shall mean waste that contains pathogens with sufficient virulence and quantity so that exposure to the waste by a human host could result in an infectious disease.

The term "Red Bag" in accordance with this invention shall be taken to mean the red colored, plastic bag that is required by regulation to be used as the container for infectious waste materials.

"Plastic" in accordance with this invention shall mean all of the organic, synthetic or processed materials including resins, foams, films, sheets and alloys (composites) that are molded, cast, extruded, drawn or laminated into objects or films.

"Pulpable materials" in accordance with this invention shall mean all of those materials that when subjected to heat, moisture or agitation or any combination of those reduces to a pulpy mass.

"Bi-directional lifting paddles" in accordance with this invention shall mean paddles utilized at spaced locations on the interior of the rotating drum that I utilize within the pressure vessel, which paddles are effective to move along the longitudinal axis of the drum, the waste material being processed, this movement taking place irrespective of the direction of drum rotation.

In accordance with this invention, the medical waste material is introduced into my novel processor, the interior of which is equipped with a rotatable cylindrically configured drum open at one equipped with a rotatable cylindrically configured drum open at one end. The interior of the rotatable cylindrical drum is equipped with a series of unique lifting paddles and directional helical flighting that, by virtue of their configurations, cause a high degree of agitation of the materials to be processed when the drum is rotated. The medical waste introduced into the processor in its undisturbed red bags is agitated by rotating the interior cylindrical drum. The medical waste is then treated by substantial heat added to the processor as the agitation of the medical waste within the processor is continued.

The addition of heat into the processor causes the red bags to become softened and distorted and, in conjunction with the effect of the very complete agitation facilitated by the lifting paddles and the helical flighting, to be opened and to gently spill their contents into the interior of the processor. The medical waste material is then treated with added moisture while continuing to agitate the waste materials which, by virtue of the effect of the lifting paddles and the helical flighting, accomplishes very thorough contacting of the medical waste materials with the added moisture.

As the process continues, the very complete contacting of the materials with the added moisture in conjunction with the agitation facilitated by the lifting paddles and the helical flighting causes the moisture absorbable materials to break down into their pulped form. The result of the breakdown of the materials into their pulped form results in a significant reduction of the overall volume of the waste materials being processed.

The addition of heat to the processor during the processing, as previously stated, allows the red bag containers holding the medical waste to become softened and in the process of agitation to spill their contents into the interior of the processor that they might be contacted with the moisture added during the processing. The addition of heat to the processor during the processing of the waste materials also speeds up the repulping of the pulpable materials.

The processing of the medical waste material continues with the addition of more heat sufficient to sterilize the now-exposed medical waste materials. The medical waste material that is being processed is held at a temperature of at least 272° F. for a period of at least 45 minutes, at a pressure of approximately 27 psig, or at a temperature of 250° F. for a period of at least 90 minutes, at a pressure of approximately 15 psig, or other combinations of pressure, temperature and time as have been proven to accomplish complete and effective sterilization of the contaminated waste.

By virtue of the added moisture, which increases the conduction of heat into the materials being processed, materials that might otherwise produce an insulating effect for themselves and on other materials are completely and quickly penetrated by the required sterilizing heat, thus avoiding the creation of pockets in which infectious materials could be protected from sufficient heat to accomplish complete sterilization.

Because of the reduction in size of the pulpable fractions of the medical wastes as they are processed, as previously described, and because the heat of the process causes the plastic fractions of the medical wastes to become heat distorted and to collapse into more compact forms, the entire amount of the medical waste is more completely agitated and therefore most completely contacted by the sterilizing heat.

After the waste materials have been processed for a sufficient amount of time at a sufficiently high temperature, a vacuum is induced on the processor to extract excess moisture from the processed materials, thereby producing a material that does not drain water from it in subsequent handling and that is less in weight as a result of the wet processing than it would be if left without dewatering as it is disposed of. The extracted water can be recovered and held for reuse in processing additional waste materials.

Instead of using high temperatures to sterilize the medical wastes, which is the preferred method, after the wastes have been spilled into the interior of the processor, a sterilizing chemical such as sodium hypochlorite or an equivalent chemical agent can be added to the processor as a part of the necessary moisture to accomplish repulping and in sufficient quantities to effect sterilization and by this addition, medical wastes can also be effectively treated.

Instead of using a vacuum system to accomplish dewatering of the processed waste materials, a mechanical dewatering system such as a dewatering press of the type that is commercially available from the Somat Corporation could be used.

The materials are then discharged from the processor for the recovery of the sterilized materials for recycling, or the sterilized materials are then subjected to grinding or other size reduction techniques so as to destroy the integrity of such materials as needles and other "sharps" that are otherwise unaffected by the processing, and render them physically harmless as well as pathologically harmless.

The preferred apparatus in accordance with this invention involves the generally cylindrical vessel mounted at a slight angle of incline with respect to the horizontal, with the preferred angle of incline being 7°, the upper end of the vessel having an opening to receive materials and the lower end of the vessel being closed. The vessel is designed with a highly effective closure device on the opening that, when closed, seals the vessel from the atmosphere to allow a buildup of pressure to occur within the vessel during its operation, or, alternatively, permits a vacuum to be maintained within the vessel by the functioning of an appropriate vacuum system.

The vessel in accordance with this invention is thus to be understood to be equipped with a generally cylindrical drum located inside the shell of the vessel at the angle of incline of the vessel and mounted upon bearings to allow the drum to be rotated inside of the vessel around its horizontal axis selectively in either direction. The upper end of the drum has an opening to receive materials to be processed, whereas the lower end of the drum is closed and watertight. The drum is equipped with novel lifting paddles and helical flighting located on its interior, to facilitate agitation and to direct movement of the materials within the drum inside of the vessel.

As the drum is rotated in accordance with my novel method, the materials in the drum are tumbled in contact with the sidewall of the drum, a distance equal to the angle of repose of the materials times the coefficient of friction of the materials times the rate of rotation of the drum. The angle of repose of the medical waste is approximately 45° and the coefficient of friction is approximately 0.2.

As the drum continues to rotate past the maximum point of the angle of repose of the materials, the materials are tumbled from the sidewall of the drum down upon itself. The angle of incline of the drum facilitates movement of the materials through the drum in that at the point of the angle of repose of the materials, the material is tumbled upon itself a distance equal to the sine of the angle of incline of the drum times the height of the material on the sidewall of the drum and in a direction concurrent with the downward slope of the angle of incline. The angle of incline also contains the material being processed in the interior of the rotating drum by virtue of the material being directed away from the opening of the drum as a consequence of the movement of the material by the rotation of the drum.

A condition known to those knowledgeable in the industry as "segregation" occurs in a rotating drum that is processing nonhomogeneous and variable sized materials. "Segregation" is the phenomenon in which a rotating drum will cause materials of different size and density to separate from each other and to stratify according to size and density, with the smallest, most dense particles migrating to the bottom of the mass of materials in the rotating drum and the largest and lightest particles rising to the top of the mass of materials in the rotating drum, with layers of intermediate sized and dense particles being sandwiched between them. The result of "segregation" is that the particles in the middle of the mass of materials are insulated from the reactive environment of the process of the drum, which in this case is heat, and are not completely sterilized.

In order to overcome the occurrence of "segregation," I install highly effective lifting paddles in preascertained locations on the interior of the rotating drum. The lifting paddles are affixed to the interior perimeter of the drum to avoid appurtenances within the drum that would prohibit material flow or that might entangle materials.

The movement of materials within the drum by the lifting paddles occurs in concert with the rotation of the drum and the angle of incline of the drum. Materials are lifted on the face of each of the lifting paddles in concert with the rotation of the drum and then are discharged from the face of the paddles as the rotation of the drum continues past the point of the angle of repose of the materials on the face of the paddles. In that a mass of materials equal to the area of the face of the lifting paddles is taken from the bottom of the mass of materials that is being processed in the rotating drum and is distributed back to the mass of materials on the top, segregation cannot occur and the agitation of the materials being processed is very thorough.

The action of the lifting paddles is subject to the movement of materials in concert with the angle of incline of the drum and the rate of rotation of the drum, as previously described, and therefore, to counteract some of the downward movement of the materials within the drum and to increase the agitation of the materials even more, the lifting paddles are designed to be affixed concurrent with the longitudinal plane of the drum in the shape of a "Y" with the bottom of the "Y" being affixed to the interior perimeter of the drum perpendicular to the sidewall of the drum and extending radially toward the centerline of the drum. The top of the "Y" is preferably affixed at an angle of 135° with respect to the perpendicular leg of the "Y" on each side of the perpendicular leg "Y" shaped lifting paddle in the plane corresponding to the diameter of the drum. Simultaneously, the top of the "Y" is preferably affixed at an angle with respect to the sidewall of the drum in the plane corresponding to the longitudinal dimension of the drum and oriented with the slope of the top of the "Y" opposing the slope of the drum.

Agitation of the materials by the active surfaces of the lifting paddles is accomplished by the tumbling and the dispersing of the materials during the rotation of the drum in either direction. As may be apparent to those skilled in the art, the materials fall randomly off the face of the lifting paddles into the mass of materials in the drum and by virtue of the opposing angle of the top of the "Y" shaped paddle with respect to the angle of incline of the drum, materials are distributed "backward," that is, in the direction that is opposite to that produced by the angle of incline during the rotation of the drum, and these materials are therefore reagitated, resulting in a very thorough mixing of the materials. As a result of this very thorough mixing, the materials being processed do not experience segregation and are completely and thoroughly exposed to the reactive environment of the drum, enabling complete sterilization to be accomplished.

As is also apparent to those skilled in the art, the size and the number of paddles oriented radially inside of the drum and the number of discharge points from the top of the sloped, "Y" shaped paddles, and the angles of incline of the drum and the angles of the top of the "Y" shaped paddles are variable and are a function of the amount of material to be processed in a given amount of time, and I am not limited to a specific set of numbers.

Movement of materials within the drum is also accomplished by helical flighting by the effect of conveyance or longitudinal motion imparted by the helix to the material contacted by the helix. The direction of movement of materials by the helix is dependent upon the direction of rotation of the drum and will be forward through the drum away from the inlet end of the drum in what I call the first rotative direction, and backward toward the inlet end of the drum in what I call the second rotative direction.

Agitation of the materials is accomplished by the directional helical flighting by the tumbling of materials during the rotation of the drum as the materials are contacted by the face of the helix. Longitudinal movement of the materials through the drum is accomplished by the angular nature of the helix in concert with the rotation of the drum. The helix is affixed to the interior perimeter of the drum in an unbroken form, and is configured to avoid appurtenances within the drum that would prohibit material flow or that might entangle materials.

As may be apparent to those skilled in the art, the rate of movement of materials by the helical flighting within the drum is dependent upon the depth of the helix, the frequency of the helix and the rate of rotation of the drum. These variables are a function of the amount of material to be processed in a given amount of time and I am not to be limited to a specific set of numbers.

In accordance with my novel method, the medical waste material, in its undisturbed red bag containers, is introduced into the processor into the internal drum opening while the drum is being rotated in the first rotative direction to facilitate filling of the drum. After the desired quantity of medical waste is placed in the processor, the closure device is closed and the waste is processed with added moisture and added heat while the drum continues to rotate in the first rotative direction. During the processing of the medical waste materials, the interaction of the forward movement of materials through the drum by the helical flighting and the angle of incline and the opposing backward movement of the materials in the drum by the unique lifting paddles results in very thorough mixing and, therefore, very complete contacting of the materials with the added moisture and the added heat for sterilization.

After processing is completed, the closure device of the vessel is opened and the drum is rotated in the second rotative direction. The backward movement of materials by the helical flighting in this rotative direction in concert with the backward movement of materials by the unique lifting paddles accomplishes the emptying of the processor of the processed materials. As is apparent to those skilled in the art, the time required to empty the processor is dependent on the depth of the helical flighting, the frequency of the helix and the rate of rotation of the vessel and these variables are a function of the amount of material to be processed in a given amount of time and I am not limited to any particular time period.

An apparatus for processing medical waste materials in accordance with this invention is therefore to be seen to comprise an elongate pressure vessel of generally cylindrical configuration having an inlet end, and a closely fitting closure member therefor. Contained in the vessel is an elongate drum of generally cylindrical configuration, mounted for rotation about its longitudinal axis, and having means for selectively driving it in either rotative direction about such longitudinal axis. The drum has an inlet end corresponding with the inlet end of the vessel, with the longitudinal axis of the drum being at a slight angle of incline to the horizontal, such that the inlet end is at a slightly higher elevation than the opposite end, which is closed and watertight.

Means are provided for agitating the medical waste within the drum by non-obstructive, helically configured means mounted at spaced locations along the interior perimeter of the drum, such that, during rotation of the drum in a first rotative direction, the helically configured means intercepts the waste materials and tends to move same forward, in the direction away from the inlet, toward the closed end of the drum, whereas during rotation of the drum in the second rotative direction, the helically configured means intercepts the waste materials and tends to move same backward in the direction toward the inlet end of the drum.

The helically configured means is preferably utilized in conjunction with a plurality of non-obstructive lifting paddles, serving with said helically configured means to effect a highly advantageous, very thorough mixing of the waste materials, the rotation of the drum in the second direction serving to effect discharge of the waste materials from the apparatus when the closure member has been opened.

I prefer to utilize means for adding controlled amounts of moisture to the interior of said the vessel during drum rotation, to enhance the penetration of heat into the moisture absorptive materials of the waste materials, thereby enhancing the effort involved in bringing about sterilization of the pathogens in the waste material. I also prefer to utilize means for agitating the waste materials within the drum by non-obstructive lifting paddles disposed along the interior perimeter of the drum, interspersed between the spacing of the helically configured means, such lifting paddles being bi-directionally configured so as to cooperate with the helically configured means, during rotation of the drum in the first rotative direction, intending to move the medical waste being processed backward toward the inlet end of the drum simultaneously with the forward movement of the waste materials as a result of the effect of the helically configured means, resulting in a highly advantageous, very thorough mixing of the waste materials, whereas during rotation of the drum in the second rotative direction, the helically configured means intercepts the waste materials and tends to move same backward, in the direction toward the inlet of the drum and simultaneously, the bi-directional lifting paddles also tend to move the waste materials backward, in the direction toward the inlet of the drum, for effecting discharge of the waste materials from the apparatus.

The lifting paddles are each equipped with a plurality of angular surfaces such that during rotation of the drum in the first rotative direction, the first plurality of surfaces of the lifting paddles serve to lift a portion of the waste materials from the mass of waste materials moving through the drum and tend to move such portion of said waste materials backward toward the inlet end of the drum simultaneously with the forward movement of the waste materials as a result of the effect of the helically configured means, with the consequence of a highly advantageous, very thorough mixing of the waste materials being obtained, leading to a very effective contacting of the waste materials with any agent added for accomplishing the sterilization of pathological contaminants, whereas during rotation of the drum in the second rotative direction, the helically configured means intercept the waste materials and tends to move same backward, in the direction toward the inlet of the drum and simultaneously, with the second plurality of surfaces of said lifting paddles also tending to move the waste materials backward, in the direction toward the inlet of the drum for effecting discharge of the waste materials from the apparatus when the closure member has been opened.

By placing a drum within a pressure vessel, I am able to have the advantages of unobstructed agitation of materials as I would have in a free-standing rotatable drum. By designing the drum to have solid, containing walls, the materials that are being processed and the additives to those materials are contained within the drum during processing. Because the drum is within a pressure vessel, the materials of construction of the drum are considerably lighter than a free-standing, rotatable drum in that the enclosing pressure vessel then has the structural integrity to withstand the forces of pressure and, in this case, the vacuum to which I will subject the waste material.

I am also interested in affixing several devices to the vessel, such as water piping, steam piping, vacuum piping, pressure controllers and other instruments for monitoring the process. On a free-standing, rotatable drum, each of these devices would require that they be affixed to the centerline of the axis of rotation of the rotatable drum. This complicates the closure devices on such a vessel and, by necessity, places these devices at the ends of the drum which in the case of pressure controllers, vacuum connections and temperature controlling instruments is usually not the appropriate location. Desirably, these devices should monitor and control the process from a location that is nearer to the point in the process where the reaction is taking place, and not adjacent to or at the opposite end of the injection of additives to the process.

Because I am placing a rotating drum within the fixed shell of a pressure vessel, I am able to attach controllers and monitors to the shell of the vessel at locations that are nearer to the reactive environment center of the process, regardless of the rotation of the drum within the vessel.

The requirement for pressure and vacuum to be induced on the system further complicates the utilization of a free-standing, rotating drum. Vacuum, in particular, requires that a device have considerable strength to keep from collapsing and this generally equates to massive components. Additionally, the requirement to introduce large objects that are generally not free-flowing and that I do not wish to reduce in size prior to their introduction to the process results in the need for closure devices that are of a large size. Because of their large size and because of the pressure and vacuum conditions of the process, such closure devices would be very difficult to handle manually. Automatic closure device operators that would be affixed to a free-standing, rotating drum would be complicated and because it is a requirement of the process to rotate the drum at a time when the closure device is open, the closure device and its operator must not interfere with the ability of the drum to rotate when the closure device is open.

By having a fixed shell with a rotating drum located inside of the shell of the pressure vessel in accordance with this invention, closure devices can be of massive size with operators that, while fixed to the shell of the pressure vessel for ease of operation, do not in any way interfere with the rotating action of the drum that is within the vessel. I prefer for the configuration of the vessel and the drum both to be generally cylindrical.

A free-standing drum, however, does offer a more advantageous design in which to utilize an inlet end and an opposite outlet end, which arrangement may be more desirable in certain situations.

The drum in accordance with this invention is inclined at a slight angle to the horizontal and the lower end of the drum is closed and watertight. The upper end of the drum is open and it is through the open end of the drum that the water and other materials are injected. The amount of water to be added corresponds to the amount of material that is to be processed and also corresponds to the amount of water that can physically be added to the drum. The water will accumulate at the lower end of the drum and will seek a maximum level that is limited by the lowest portion of the upper, open end of the drum.

Because the drum is open on one end, the drum experiences the same conditions of pressure, temperature and vacuum as that experienced in the pressure vessel. Water and steam are injected into the opening of the drum by piping that is permanently fixed and supported to intrude into the opening of the drum without having to touch the drum.

All of the lifting paddles are oriented with their angular portions sloped in the same consistent direction to cause a "backward" movement of materials toward the opening of the drum, in opposition to the movement of materials by the helix when the drum is being rotated in the first rotative direction and, by virtue of a reciprocal angular portion on the opposite side of the paddles, the materials are caused to be moved "backward" toward the opening of the drum in concert with the movement of the materials by the helix when the drum is rotating in the second rotative direction.

I install the novel lifting paddles at locations that are staggered from each other from section to section, to effect a more even lifting of materials being processed within the drum and a more thorough mixing of those materials. This effective positioning of the novel lifting paddles also causes a more even loading of forces on the drive and support mechanisms of the drum by virtue of the more even lifting of the materials by the paddles.

The diameter of the drum needs to be sufficient to accept a bag of material to be processed with an additional space of approximately 40% of the volume of the interior diameter of the drum left vacant to allow materials to fall and to mix within the drum as it rotates. Additional processing capacity is then added to the processor by increasing its length. The ratio of diameter to length is variable and depends upon the amount of material to be processed in a given amount of time in concert with the size and frequency of the agitation mechanisms of the drum to insure complete mixing of materials.

The pressure vessel is supported by structural steel supports designed to transfer the weight of the processor and its contained materials to the foundation under the processor, which foundation has a sufficiently wide base to give the vessel stability. The rotating drum within the shell of the vessel will transfer its forces to the carrier and support bearings which in turn will transfer that load into the shell of the vessel and become a part of the load supported by the structural supports of the shell and transferred to the foundation below the processor.

The rotation of the drum within the shell will have no other influence on the support mechanisms of the vessel or the stability of the vessel that is not accommodated by the structural supports.

Advantages of this design are:
1. The very unique lifting paddles that by virtue of the angular surfaces, cause a "backward" flow of materials from the face of the paddles in either rotative direction effecting a very complete mixing of materials.
2. Lighter materials of construction for the rotating components under conditions of pressure and vacuum.
3. Closure devices that, although massive, are fixed to the stationary shell of the vessel and are easy to operate.
4. Piping systems located to monitor and to control the process that are nearer to the center of the reaction of the process.

It is therefore a main object of my invention to provide a novel method and an apparatus for accepting packaged medical waste and in a single unit operation, utilizing sufficiently high temperature as to achieve complete pathogen destruction.

It is another object of this invention to provide a novel processing vessel containing novel components in its interior that are effective in either direction of rotation, and by the use of which, an extremely thorough mixing of materials is accomplished.

It is yet another object of this invention to provide a novel method for greatly reducing the bulk of waste materials by accomplishing a very thorough mixing of these waste materials in the presence of substantial heat and moisture, resulting in a pulping of the pulpable materials and a softening and a collapsing of plastic materials into a more compact form.

It is still another object of this invention to provide a rotating drum disposed inside a pressure vessel, on the interior sidewalls of which drum are disposed a plurality of unique, bi-directional lifting paddles that are effective for bringing about a very thorough mixing of the medical wastes being processed, irrespective of the direction of rotation of the drum.

It is yet still another object of this invention to provide novel method and apparatus for sterilizing medical waste by the use of substantial quantities of water and intense heat maintained over a sufficient period of time as to penetrate all parts of the medical waste, with this being followed by the application of a vacuum to remove excess water before the pulped waste is removed from the rotating drum contained in the vessel.

These and other objects, features and advantages will be more apparent from a consideration of the appended drawings and description.

DETAILED DESCRIPTION

Figure 1:
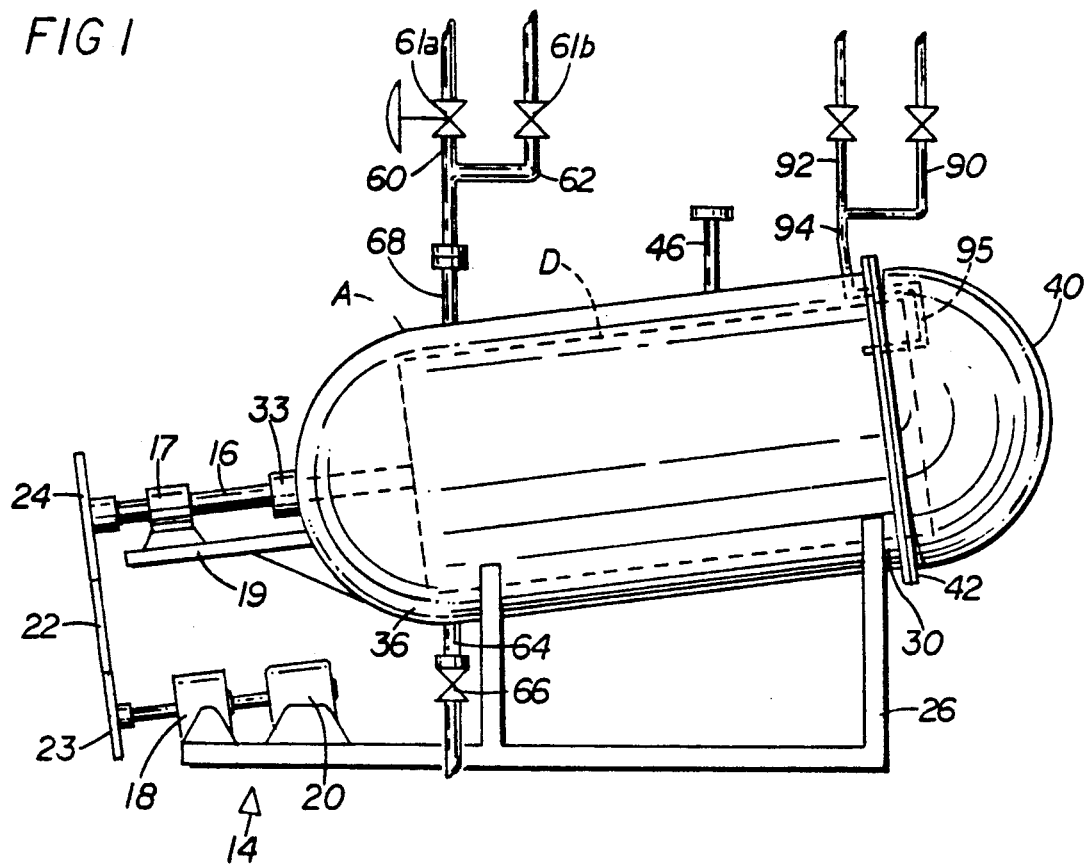
FIG. 1 is a side elevational view of the novel pressure vessel I use for elimination of pathogens from medical waste, such vessel containing a rotating drum.
Figure 2:
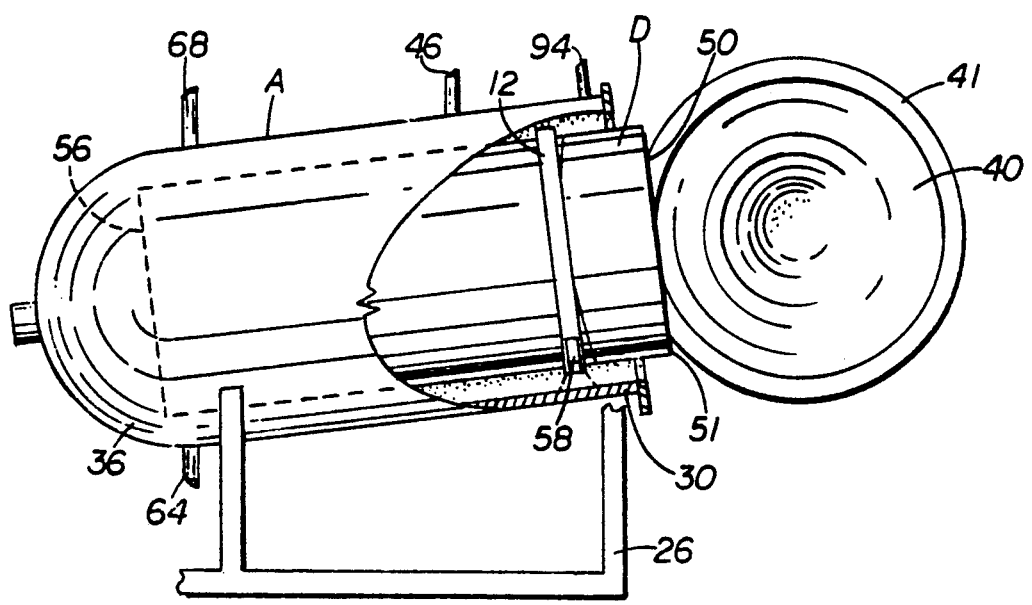
FIG. 2 is a view bearing a definite relationship to FIG. 1, with part of the vessel broken away to reveal the rotating drum, and showing the vessel's closure member in the open position.

With initial reference to FIG. 1, it will there be noted that I have revealed the exterior of my novel apparatus particularly designed for the processing of medical waste materials and the like, the use of which also involves a novel method.

This invention includes the advantageous utilization of a heavy walled processing vessel A that is generally cylindrical in configuration. Heavy walls are used in the construction of vessel A in order that it can operate under conditions of high internal pressure as well as on occasion, under vacuum conditions. The vessel A is mounted in a non-rotatable manner on a sturdy stationary support 26, having a sufficiently wide base as to give ample stability. The support 26 preferably utilizes structural steel members designed to effectively transfer the weight of the processor and its contained materials to the foundation under the processor.

The rotating drum about to be described, that I utilize within the shell of the vessel A, transfers its forces to carrier and support bearings, which in turn transfer that load into the shell of the vessel A and become a part of the load supported by the structural supports of the shell, and thus transferred to the foundation below the processor.

A closure device or dome shaped door 40, provided with a seal 41, is hingedly mounted adjacent the inlet 30 of the vessel A so that substantial pressure or a vacuum can be established inside the vessel at selected times, as mentioned previously.

Located inside the non-rotating vessel A is a generally cylindrical drum D mounted so as to be rotatable in either direction on its axis, which axis is coincident with the axis of the vessel A. Drum D is provided with a riding ring or support ring 12 adjacent its front end 50, with rollers or trunnion bearings 58 being positioned on the interior of vessel A to contact the ring 12, and thus provide support for the front end 50 of the drum D. The front end 50 of the drum D is open, whereas the rear or lower end 56 of the drum is closed and watertight.

Affixed to the rear or lower end 56 of the drum D is drive shaft 16, which is arranged to support the rear end of the drum D and drive it in rotation. The shaft is rotatably supported by roller or ball bearings 17 that are in turn supported from a structural member 19 attached to the vessel A. This support arrangement is designed to fix the location of the drum D insofar as its horizontal positioning within the vessel A is concerned.

The drive shaft 16 of the drum D penetrates the shell of the vessel A and is sealed from the atmosphere by a seal 33 of the type manufactured by John Crane-Houdaille, Inc. of Morton Grove, IL to enable a selected pressure or a selected vacuum to be maintained from time to time within the vessel A, and of course within the drum D.

The typical rate of rotation for the drum D is between 2 and 30 rpm and preferably approximately 15 rpm to facilitate a uniform loading of forces on the drive mechanism 14 utilized for driving the drum in rotation.

Figure 3:
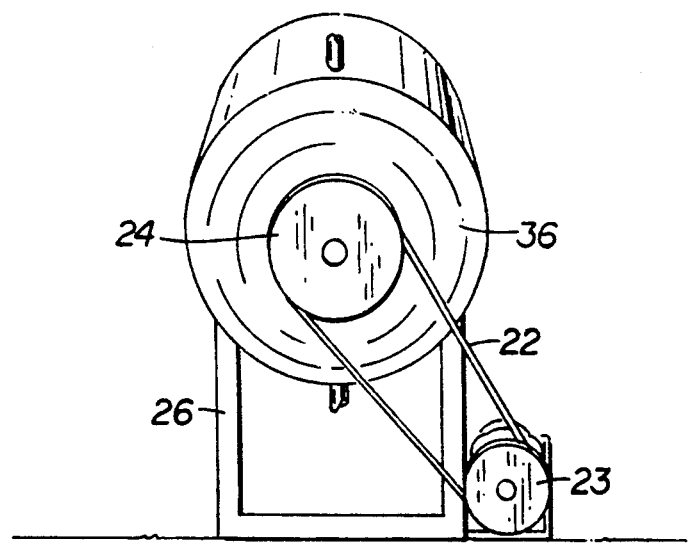
FIG. 3 is an end view of the lower end of the pressure vessel, this view revealing the drive means I prefer to use for driving the drum in rotation.
Figure 4:
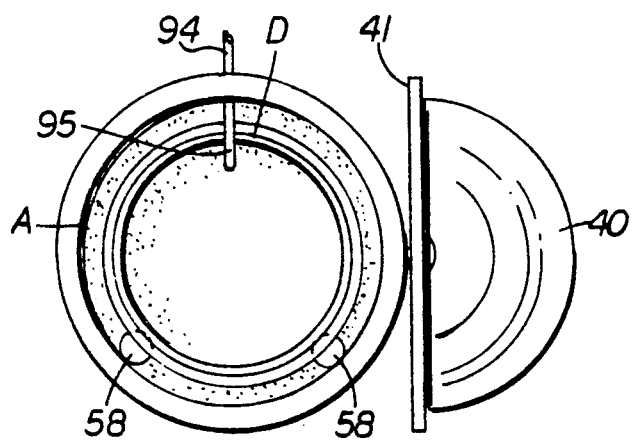
FIG. 4 is an end view of the upper end of the vessel, showing sealing means as well as the open end of the rotating drum.

The drum D is capable of being rotated in either direction on its horizontal axis by means of the drive assembly 14 depicted in FIG. 1 that may, for example, utilize a reversible electric motor 20 and suitable reduction gearing 18 connected to the drive shaft 16 of the drum to turn the drum D in the selected direction. I prefer to use a heavy duty chain 22 passing over sprockets 23 and 24 for transferring the rotation of the motor to the drive shaft, in an arrangement familiar to those knowledgeable in the art, as depicted in FIGS. 1 and 3.

By placing the drum D within the pressure vessel A, I am able to have the same advantages of unobstructed agitation of materials as I would have had in a free-standing rotatable drum. By designing the drum to have adequate containing walls, the materials that are being processed and the additives to be inserted into those materials are contained within the drum during processing. Because in accordance with this invention the drum is disposed within a pressure vessel, the materials of construction of the drum are considerably lighter than are required for a free-standing, rotatable drum, which would have required the structural integrity to withstand the forces of pressure as well as the forces associated with the vacuum that will be utilized from time to time in the process.

Along the lines of the arrangement set forth in my allowed copending patent application Ser. No. 321,563, now U.S. Pat. No. 4,974,781, the interior of drum D is equipped with a series of lifting paddles 70 and a helical flighting 80 to facilitate agitation and movement of waste materials as a consequence of rotation of the drum D. The lifting paddles used for the instant invention and the flighting will shortly be described in more detail.

Vessel A, in accordance with this invention, is preferably operated on an incline. The preferred angle of incline is 7° from the horizontal, with the front or inlet end 30 being higher than the closed lower end 36 of the vessel. The angle of incline aids in containing the materials to be processed within the drum D in that the medical waste and other such materials will be moved through the drum D toward the back end, at least partly under the influence of gravity as the drum is rotated.

I am not to be limited to any particular size of drum D, but it is to be noted that a device in accordance with this invention utilizing a drum approximately ten feet long is of a size that can be effectively utilized in a hospital or a large medical office, for example, where it is extremely convenient to be able to get rid of contaminated medical waste on the premises, making unnecessary the shipment of the contaminated waste to another location for disposal. In other words, a smaller sized version of a waste processor in accordance with this invention could take the form of a unit that could be placed within a relatively limited area, to handle medical type waste materials generated therein.

It is obviously possible to build larger units in accordance with the teachings of this invention, to perform large scale operations, and by the foregoing mention of a processor of a size to be used in a hospital I do not intend to limit the largeness or smallness of any processor, except that the diameter of the vessel should be sufficiently large as to accept materials upon which a prior size reduction has not taken place. Any combination of reasonable diameters and lengths could be utilized in accordance with this invention, limited only by practicality.

In terms of size practicality, the primary limit on size would be the limitations that are imposed on items that are shipped on trucks over roads and highways. This limit is 12 feet in diameter and 50 feet long, and even this size requires special permits for oversize shipment. Above this size, shipment by standard means becomes impractical. On the other hand, the fabrication of units of virtually unlimited size can be constructed on the site of a proposed operation, accomplished by utilizing special fabrication techniques.

Returning to the details of a preferred embodiment of my invention, the lifting paddles 70 are mounted on the interior of the drum D and are arranged so as to minimize any obstruction of flow of materials within the drum. The lifting paddles are distributed in sections along the horizontal dimension of the drum, as shown in FIG. 5, and are staggered at approximately 45° intervals from one section to the next.

Figure 5:
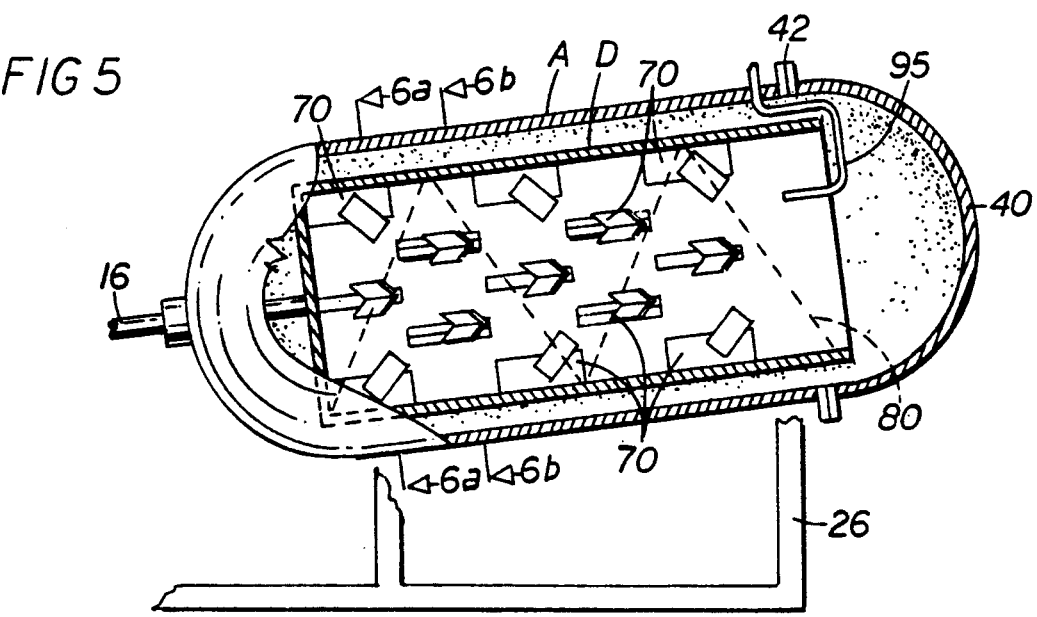
FIG. 5 is a side elevational view in which the sidewalls of both the pressure vessel and the rotating drum are broken away to reveal the utilization of my novel lifting paddles disposed in a spaced array around the interior of the rotating drum, with the location of the helical flighting being indicated by the use of dashed lines.
Figure 6A:
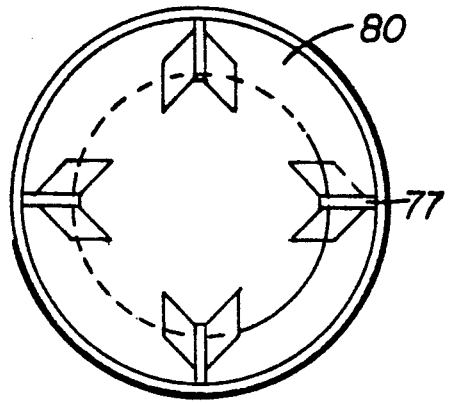
FIG. 6a is a cross sectional view taken along lines 6a—6a in FIG. 5.
Figure 6B:
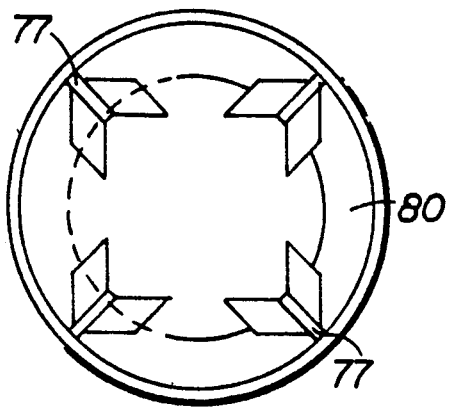
FIG. 6b is a cross sectional view taken along lines 6b—6b in FIG. 5.
Figure 7:
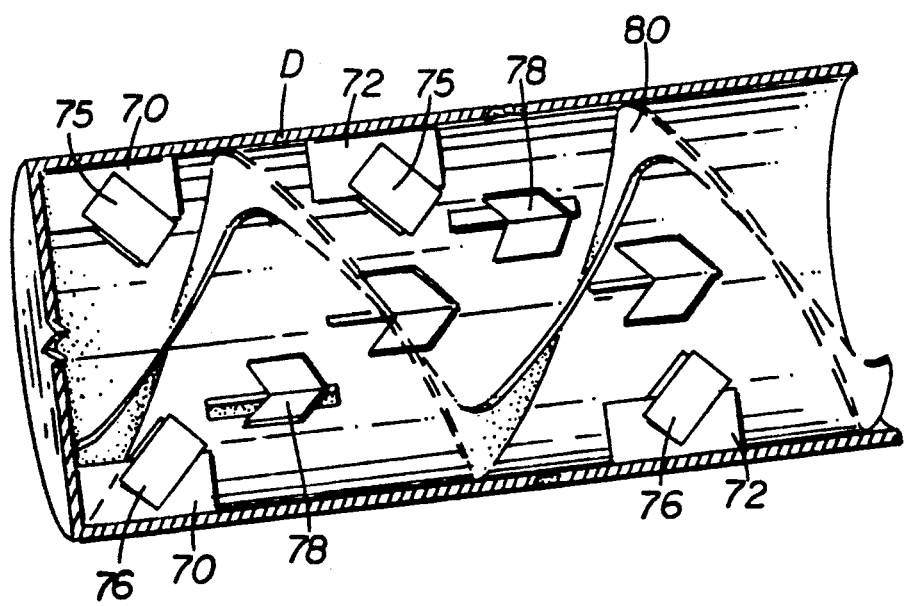
FIG. 7 is a view somewhat schematically indicating the relationship of the lifting paddles to the helically arrayed flighting disposed around the interior surface of the rotating drum.

The lifting paddles 70 are affixed to the interior perimeter of the drum D perpendicular to the shell of the drum, as shown in FIGS. 6a and 6b, and are oriented lengthwise to correspond with the longitudinal dimension of the drum, as is shown in FIGS. 5 and 7.

Figure 8:
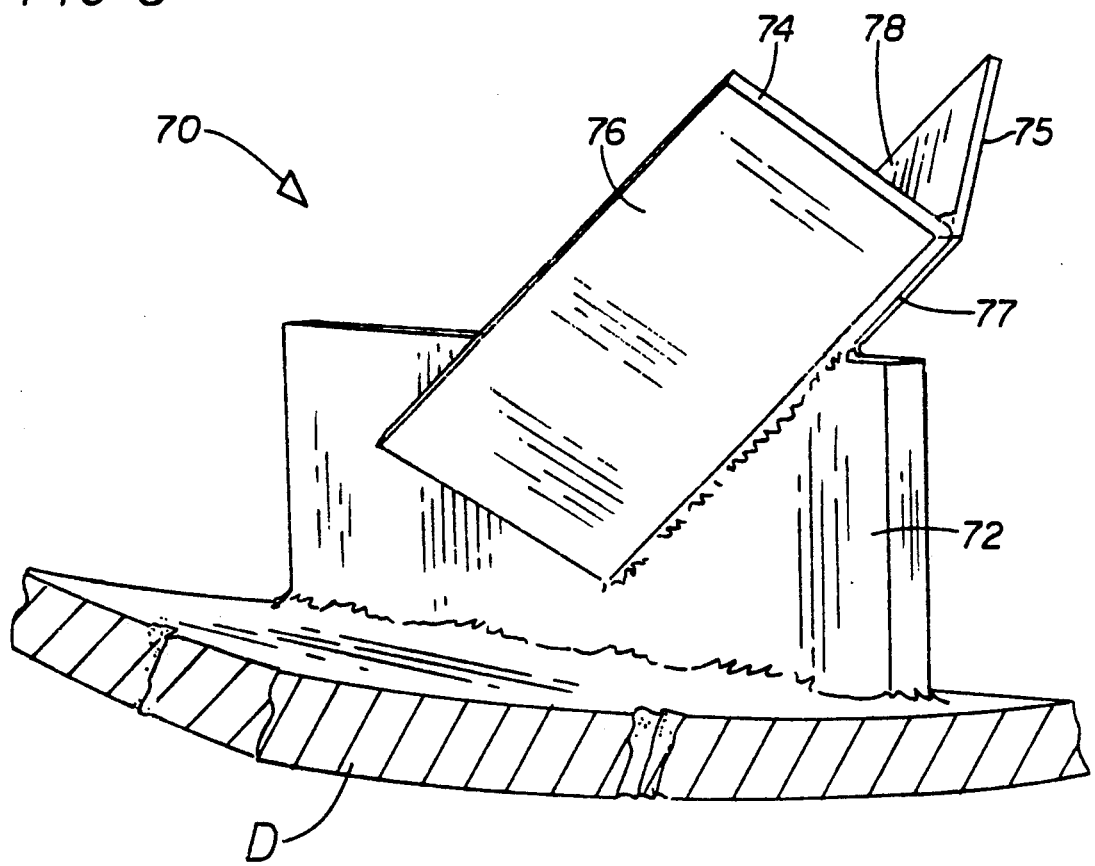
FIG. 8 is a view to a substantially enlarged scale of a typical lifting paddle in accordance with this invention, with the adjacent portion of the drum in cross section, and the closed end of the drum being toward the left as viewed in this figure.

As best seen in FIG. 8, the perpendicular leg 72 is affixed to the interior sidewall of the drum, and the angled member 74 is affixed at its midline 77 to the radially inner portion of the perpendicular leg. The angled member 74 has external surfaces 75 and 76, with surface 75 being at an angle of approximately 45° from the perpendicular leg 72 of the lifting paddle, and surface 76 being at a like angle to the leg 72. I prefer to utilize the midline 77 of the angled member 74 at an angle of approximately 52° with respect to the interior surface of the drum D, and as shown in FIG. 8, the midline 77 is placed in a direction that is toward the higher end of the drum D. Stated somewhat differently, the interior portions 78 of the lifting paddles face the closed end 56 of the drum D, which is to the left as view from the perspective of FIG. 8.

In the preferred embodiment, the angle of incline of the drum is 7° with respect to the horizontal, so the angle of incline of the angular portions 75 and 76 of the lifting paddle is 52° with respect to the shell wall of the drum D, and this results in the angular portions 75 and 76 of the lifting paddle operating at an angle of 45° with respect to the horizontal.

The helical flighting 80 is affixed to the interior perimeter of the drum D so as to minimize obstruction of flow of materials within the drum, and preferably at a frequency corresponding to one complete cycle of the helix in a distance equal to the diameter of the drum, measured along the length of the drum. The angularity of the helical flighting is such that when the drum D is rotated in what I call the first rotative direction, the materials to be processed are moved forward, toward the closed lower end 56 of the drum, whereas rotation of the drum in the second rotative direction causes the materials to be moved backward toward the inlet opening 50 of the drum. The helical flighting is continuous, meaning that occasional lifting paddles 70 must be eliminated at certain locations in order to make fabrication possible.

As is obvious to those skilled in the art, the size and frequency of the lifting paddles, the angle of incline of the drum and the rate of rotation of the drum are variable and are a function of the required rate of movement of materials within the drum and the amount of material to be processed in a given amount of time.

The diameter of the drum needs to be sufficient to accept a selected quantity of material to be processed, with an additional space of approximately 40% of the volume of the interior diameter of the drum needed to remain vacant to allow materials to fall and to mix within the drum as it rotates. In a design of this type of device, additional processing capacity is added to the processor by increasing its length. The ratio of diameter to length is variable and depends upon the amount of material to be processed in a given amount of time in concert with the size and frequency of the agitation mechanisms of the drum to insure complete mixing of materials.

As will be discussed at length hereinafter, I utilize several devices for monitoring and controlling the process, such as water piping, steam piping, vacuum piping, pressure controllers and other needed instruments. In using a free-standing, rotatable drum, each of these devices requires that they be affixed to the centerline of the axis of rotation of the rotatable drum, which complicates the closure devices on such a vessel and, by necessity, places these devices at the ends of the drum. In the case of pressure controllers, vacuum connections and temperature controlling instruments, this is not an appropriate location. Rather, devices of this type should monitor and control the process from a location that is nearer to the point in the process where the reaction is taking place, and not adjacent to or at the opposite end of the injection of additives to the process. These factors have contributed to the decision I made to utilize a pressure vessel in which a rotating drum is utilized.

Another reason for the decision involves the fact that the requirement for pressure and vacuum to be induced in a system concerned with pathogen destruction further complicates the utilization of a free-standing, rotating drum. Vacuum, in particular, requires that the selected device have considerable strength to keep from collapsing, and this generally equates to massive components, requiring considerable horsepower if such components are to be driven in rotation.

Additionally, the requirement to introduce large objects that are generally not free-flowing, that are not conveniently reduced in size prior to their introduction to the process necessitates that the closure device be of large size. Because of their large size and because of the pressure and vacuum conditions of the process, the closure devices would be very difficult to handle manually. Automatic closure device operators that would be affixed to a free-standing, rotating drum would be complicated and because it is a requirement of the instant process to rotate the drum for a time period during which the closure device is open, the closure device and its operator must not interfere with the ability of the drum to rotate under these circumstances.

With reference to FIG. 1, the vessel A is equipped with piping 90 for the selective addition of steam and piping 92 for the selective addition of water, with suitable valves being utilized in order to control the flow. The steam piping and the water piping are combined into a single injection pipe 94 as shown in FIG. 1, enabling steam and water to be conducted through the sidewall of the vessel A and then injected into the open end of the drum D, through curved fixed pipe 95.

Figure 9:
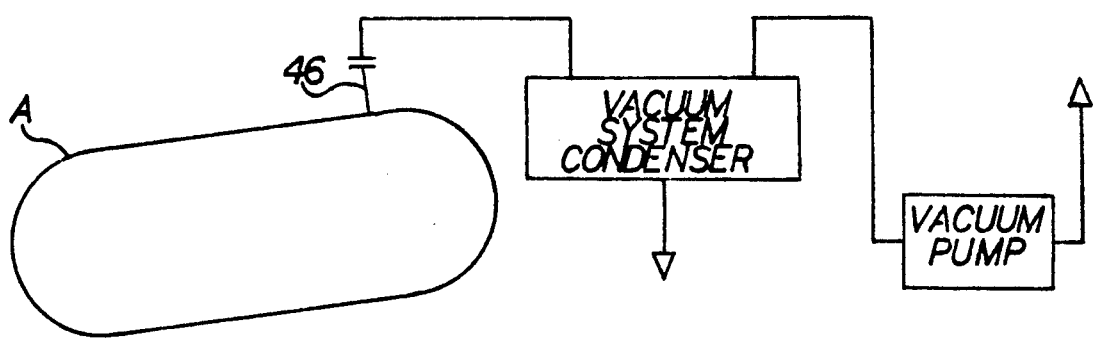
FIG. 9 is a schematic of the vacuum system used.

During one phase of the operation of my device, vacuum is induced into the vessel A by a vacuum system such as the type manufactured by Nash Engineering Company of Norwalk, CT or Croll-Reynolds Company, Inc. of Westfield, NJ, connected to the vessel by vacuum connection 46; note FIG. 9.

In accordance with my novel method, medical waste is carried by a suitable conveyor and introduced through the inlet opening 30, when the door 40 has been moved to the open position, and into the open end 50 of the drum D. Inasmuch as medical waste is typically packaged in red bags of a particular size and may also contain an assortment of materials varying in size, shape and density, and which may not necessarily be free flowing, the inlet opening 30 in the vessel A and the opening 50 into the drum are large enough and without obstructions so as to allow previously unprocessed medical waste to be directly introduced into the processor.

The drum D is rotated in the first rotative direction while medical waste is being conveyed into the drum, and, by virtue of the helical flighting 80 and the angle of incline of the drum, a sufficient amount of the material, though not free flowing, will be loaded into the drum for processing.

When the drum D has been filled with a sufficient amount of material to be processed, the closure device 40 is closed and is secured by a locking ring 42, such as the type manufactured by the Klinge Products Company of Denmark.

I typically add substantial quantities of water to the medical waste to be processed, this being accomplished by injecting water through pipe 92, such that sufficient water is brought into contact with the material in the drum, via the curved stationary pipe 95. Moisture is usually added to accomplish a moisture content of between 30% and 90% in the moisture absorbable materials, with approximately 75% being the optimum. The drum D is ordinarily rotated in the first rotative direction during the water addition to enhance the contact of the waste materials with the added moisture.

In the first rotative direction, assumed to be clockwise when viewed from the open end of the drum, material is intercepted by the directional flighting 80 and is moved through the drum toward the back or closed lower end 56 of the drum. Simultaneously, the bi-directional lifting paddles 70, by virtue of the angular portion of each paddle, direct a portion of the waste material counter-currently toward the inlet end of the drum as each of the paddles comes in contact with the material during the rotation of the drum. This simultaneous backward and forward movement of materials within the drum by the action of the helical flighting 80 and the surfaces 76 of the novel lifting paddles 70 during the rotation of the drum D in the desired direction results in a highly advantageous and a very complete agitation of the materials being processed. Because of these actions and the added moisture, the repulping of the pulpable materials of the waste materials is very effectively accomplished.

I prefer to regard the surfaces 76 as the first portions, and the surfaces 75 of the paddles as the second portions.

Heat is added to the vessel during the processing of the waste materials. In this case, steam may be advantageously added to the vessel by steam piping 90 and injected into the waste materials by injection piping 94 while the drum is being rotated in the first rotative direction; note FIG. 1. As previously described, the addition of heat causes the plastic red bags to become softened and to open and spill their contents into the drum while the drum is being rotated, thus allowing the materials that were in the bags to be completely agitated and contacted with the added moisture and added heat. Desired pressure is maintained in the vessel A by suitable use of the valves of the pressure control system associated with the pressure pipe 60 and the vent connection 62. Valve 61a controls the pressure pipe, and valve 61b the vent pipe 62. Pipe 68 forms the connection to the interior of vessel A. If desired to add a sterilizing agent, sodium hypochlorite or the like can be added as a liquid or a vapor into the steam line, or alternatively into the water line.

A temperature of at least 272° F. is maintained for a period of at least 45 minutes at a pressure of approximately 27 psig during the processing of the waste materials to accomplish the sterilization of the waste materials. Heat is added by the injection of steam to attain the required temperature, this being accomplished from the previously described piping, and pressure resulting from the injection of the steam is controlled and maintained by the pressure control system connected to the vent piping.

Because of the added moisture, and the very complete agitation, the required heat needed to accomplish sterilization of the medical waste materials is more able to be transferred into those materials, such that very effective sterilization is accomplished.

When processing has been completed, the steam injection to the system is shut off and the vacuum system depicted in FIG. 9 is turned on while continuing to rotate the drum in the first rotative direction. As a vacuum is induced on the vessel, moisture is withdrawn from the processed materials through vacuum connection 46 and into the vacuum system, and collected for reuse in future processing or for discharge.

The amount of water that is added to the process will be absorbed by the moisture absorbable materials that are in the waste during the processing and will not exist in a pool in the vessel as the vacuum is being applied.

Additionally, as the vacuum is induced on the system, the temperature of the boiling point of the water is reduced and the water is vaporized and withdrawn from the system into the vacuum system. The greater the intensity of the vacuum that is induced on a system, the greater is the decrease in the boiling point of the water that is exposed to the vacuum in the system. For instance, at approximately 5 lbs. of absolute pressure, with 14.7 lbs. of absolute pressure being equal to the atmospheric pressure and 0 lbs. of absolute pressure being a perfect vacuum, water will boil at approximately 162° F. and at approximately 1 lb. of absolute pressure, water will boil at approximately 102° F.

Drying techniques such as vacuum evaporation and freeze-drying utilize this phenomenon to accomplish low heat drying.

In that I use high temperatures during the processing and these temperatures are significantly higher than the atmospheric boiling point of water, when I induce a vacuum on the system, I cause a rapid evolution of moisture to vapor and therefore a rapid drying effect of the materials that are in the processor. Another benefit of the evaporative effect of moisture loss in this manner is the resulting cooling of the materials that have been processed that they may more easily be handled in subsequent operations as we have described in the text. Under these conditions, even pooled water will evolve into vapor and be withdrawn from the system.

I prefer to use a vacuum connection at the top of the vessel in that the evolving vapor, as it is being withdrawn from the system, can act as a carrier gas and, by its velocity, can carry light particles with it out of the vessel and into the vacuum system and potentially clog it. By placing the nozzle at the top of the vessel, gravity will make this action less likely. The installation of the nozzle is also at a point that causes a torturous path to be followed by the vapor, further preventing particles from being carried into the vacuum system in that a change in direction of a carrier gas stream will cause the deposition of particles that are being carried from the gas stream.

It is also to be noted that the installation of the nozzle on the top of the shell of the vessel causes the vapor evolving from the materials in the drum to travel out of the opening 50 of the drum and to turn back along the interior perimeter of the shell of the vessel to reach the nozzle and by virtue of the change in direction of the vapor stream at the opening of the drum, to deposit particles that may be carried in the vapor stream at the opening of the drum.

As the vacuum is induced and the moisture is withdrawn from the system, the processed materials are cooled from the temperature of sterilization to a lower, more manageable temperature for further handling, and from a level of moisture required for effective sterilizing heat penetration to a drier, more manageable moisture level. As is obvious to those skilled in the art, the coolness and the dryness of the processed materials are variables and are dependent on the subsequent requirements of further handling in a particular operation. In this case, a dryness of approximately 20% moisture in the moisture absorbable materials and a corresponding temperature of approximately 200° F. is preferred.

If additional cooling needs to be accomplished beyond that attained as a consequence of moisture removal, air can be drawn into the system through vent connection 62 while the vacuum system continues to operate and, in this manner, additional cooling of the materials can be accomplished.

When the required temperature and dryness are accomplished, the vacuum system is turned off and the rotation of the drum is stopped. The closure device 40 is opened and the drum D is rotated in the second rotative direction. In the second rotative direction, assuming counter-clockwise rotation, the processed waste materials are intercepted by the helical flighting 80 and are directed toward the inlet end of the drum D by the action of the helical flighting. As the drum continues to rotate, the processed materials are also lifted and directed toward the inlet end of the vessel by the surfaces 75 of the "Y" shaped lifting paddles 70, as previously described.

As should now be clear, the angular surfaces 75 and 76 on each side of the perpendicular surface of the paddles, function in an equal manner in either rotative direction, assisted of course in each instance by the vertically disposed member 72.

It is to be noted that my novel lifting paddles 70 are always functioning in a counter-current manner with respect to the helical flighting 80 during processing, with the surfaces 76 serving in a primary manner at such time. Only after the waste materials have been fully processed do I reverse the rotative direction of the drum D, so as to enable the helical flighting to discharge the material out over the lip 51 of the drum into a suitable discharge system. At this time of discharge, the surfaces 75 of the paddles 70 serve in a primary manner, in effect cooperating with the action of the helical flighting 80.

The processed materials are thus discharged from the vessel by the combined action of the helical flighting 80 and the surfaces 72 and 75 of the lifting paddles 70 during the rotation of the drum D in the second rotative direction. Because the outer lip 51 of the drum protrudes beyond the outer rim of the vessel A, the discharged processed materials fall clear of the vessel. By virtue of the repulping of the pulpable materials, the volume of the processed waste material is reduced to approximately ⅓ of its original volume.

The rate of discharge of the processed materials, as is apparent to those skilled in the art, is dependent on the rate of rotation of the drum, the size and frequency of the helical flighting, and the size and number of the lifting paddles and these variables are dependent on the amount of material to be processed in a given amount of time and I am not limited to a single combination of these variables.

Drain connection 64 is equipped with a suitable valve 66, which can be opened to enable moisture to be drained from the shell (pressure vessel A) upon excess accumulation thereof.

The processed materials are then directed to screeners for the separation and recovery of recyclable materials and further to compactors or to shredders for the destruction of the remaining materials such as sharps that might be present, that they may safely be disposed of.

Other methods and equipment for the separation of component fractions from the processed materials or the further processing of the processed materials for the destruction of the residual material such as sharps that may be present in the processed materials are apparent to those skilled in the art and these techniques may also be used for product recovery from the processed materials or for disposal of the residue from the processed materials.

I claim:

1. An apparatus for processing medical waste materials comprising an elongate pressure vessel of generally cylindrical configuration having an inlet end, and a closely fitting closure member therefor, said vessel containing an elongate drum of generally cylindrical configuration mounted for rotation about its longitudinal axis, said drum having means for selectively driving it in either rotative direction about such longitudinal axis, said drum having an inlet end corresponding with the inlet end of said vessel, with the longitudinal axis of said drum being at a slight angle of incline to the horizontal, such that the inlet end is at a slightly higher elevation than the opposite end, means for agitating the medical waste within the drum by non-obstructive, helically configured means mounted at spaced locations along the interior perimeter of said drum, such that, during rotation of the drum in a first rotative direction, said helically configured means intercepts the waste materials and tends to move same forward, in the direction away from the inlet end of said drum, whereas during rotation of the drum in the second rotative direction, said helically configured means intercepts the waste materials and tends to move same backward in the direction toward the inlet end of the drum, said helically configured means being utilized in conjunction with a plurality of non-obstructive lifting paddles, serving with said helically configured means to effect a highly advantageous, very thorough mixing of the waste materials, the rotation of said drum in said second direction serving to effect discharge of the waste materials from said apparatus when said closure member has been opened.

2. The apparatus for processing medical waste materials as defined in claim 1 in which means are provided for adding controlled amounts of moisture to the interior of said vessel, such moisture serving to enhance the penetration of heat into the moisture absorptive constituents of the waste materials, thereby enhancing the effort involved in bringing about sterilization.

3. The apparatus for processing medical waste materials as defined in claim 1 in which means are provided for adding controlled amounts of moisture to the interior of said vessel, such moisture serving to increase the density of the moisture absorptive materials of said waste materials so that during the mixing procedure, repulping of the moisture absorptive materials can be accomplished, resulting in a decrease in the volume of the waste materials.

4. The apparatus for processing medical waste materials as defined in claim 1 in which means are provided for adding controlled amounts of heat to the interior of said vessel, such heat serving to soften plastic film containers enclosing the waste materials, causing them to rupture and to gently spill their contents into the interior of the vessel and exposing them to the reactive environment of the interior of the vessel, thereby enhancing the effort involved in bringing about sterilization.

5. The apparatus for processing medical waste materials as defined in claim 1 in which means are provided for adding controlled amounts of steam to the interior of said vessel, such steam causing the plastic containers for the medical waste to become softened, and to spill their contents into the interior of said drum.

6. The apparatus for processing medical waste materials as defined in claim 1 in which said vessel is designed to withstand internal pressure during one phase of the sterilization procedure, and a vacuum condition during another phase of the sterilization procedure, said closure member having means for sealing said inlet end of said vessel so that the interior of said vessel can be maintained at a pressure above atmospheric pressure during said one phase, and so that the interior of said vessel can be maintained at a pressure below atmospheric pressure during said other phase.

7. The apparatus for processing medical waste materials as defined in claim 1 in which means are provided for adding controlled amounts of steam to the interior of said vessel, such steam causing sterilization of the waste materials to be accomplished.

8. The apparatus for processing medical waste materials as defined in claim 7 in which means are provided for controlling the pressure within said vessel within operational parameters during times of such steam injection.

9. The apparatus for processing medical waste materials as defined in claim 1 in which said drum is inclined at a slight angle to the horizontal, with said inlet end being higher.

10. The apparatus for processing medical waste materials as defined in claim 1 in which said non-obstructive helically configured means is affixed in an unbroken manner along to the interior perimeter of said rotatable drum, for effecting movement of the waste materials within said drum.

11. The apparatus for processing medical waste materials as defined in claim 1 in which said non-obstructive lifting paddles are affixed to the interior perimeter of said rotatable drum to effect movement and agitation of the waste materials within said drum in opposition to the movement of the waste materials by said helically configured means at selected times, and to function in conjunction with the movement of the waste materials by said helically configured means at selected other times.

12. An apparatus for processing medical waste materials comprising an elongate pressure vessel of generally cylindrical configuration having an inlet end, and a closely fitting closure member therefor, said vessel containing an elongate drum of generally cylindrical configuration mounted for rotation about its longitudinal axis, said drum having means for selectively driving it in either rotative direction about such longitudinal axis, said drum having an inlet end corresponding with the inlet end of said vessel, with the longitudinal axis of said drum being at a slight angle of incline to the horizontal, such that the inlet end is at a slightly higher elevation than the opposite end, means for agitating the medical waste within the drum by non-obstructive, helically configured means mounted at spaced locations along the interior perimeter of said drum, such that, during rotation of the drum in a first rotative direction, said helically configured means intercepts the waste materials and tends to move same forward, in the direction away from the inlet end of said drum, whereas during rotation of the drum in the second rotative direction, said helically configured means intercepts the waste materials and tends to move same backward in the direction toward the inlet end of the drum, means for agitating the waste materials within the drum by non-obstructive lifting paddles disposed along the interior perimeter of the drum interspersed between the spacing of said helically configured means, said lifting paddles being bi-directionally configured so as to cooperate with said helically configured means, during rotation of said drum in the first rotative direction, intending to move the medical waste being processed backward toward the inlet end of said drum simultaneously with the forward movement of said waste materials as a result of the effect of said helically configured means, resulting in a highly advantageous, very thorough mixing of the waste materials, whereas during rotation of the drum in the second rotative direction, said helically configured means intercepts the waste materials and tends to move same backward, in the direction toward the inlet of the drum and simultaneously, said lifting paddles also tend to move the waste materials backward, in the direction toward the inlet of said drum, for effecting discharge of the waste materials from the apparatus.

13. The apparatus for processing medical waste materials as defined in claim 12 in which means are provided for adding controlled amounts of moisture to the interior of said vessel, such moisture serving to enhance the penetration of heat into the moisture absorptive materials of the waste materials, thereby enhancing the effort involved in bringing about sterilization.

14. The apparatus for processing medical waste materials as defined in claim 12 in which means are provided for adding controlled amounts of moisture to the interior of said vessel, such moisture serving to increase the density of the moisture absorptive materials of said waste materials so that during the mixing procedure, repulping of the moisture absorptive materials can be accomplished, resulting in a decrease in the volume of the waste materials.

15. The apparatus for processing medical waste materials as defined in claim 12 in which means are provided for adding controlled amounts of heat to the interior of said vessel, such heat serving to soften plastic film containers enclosing the waste materials, causing them to rupture and to gently spill their contents into the interior of the vessel and exposing them to the reactive environment of the interior of the vessel, thereby enhancing the effort involved in bringing about sterilization.

16. The apparatus for processing medical waste materials as defined in claim 12 in which means are provided for adding controlled amounts of steam to the interior of said vessel, such steam causing the plastic containers for the medical waste to become softened, and to spill their contents into the interior of said drum.

17. The apparatus for processing medical waste materials as defined in claim 12 in which said vessel is designed to withstand internal pressure during one phase of the sterilization procedure, and a vacuum condition during another phase of the sterilization procedure, said closure member having means for sealing said inlet end of said vessel so that the interior of said vessel can be maintained at a pressure above atmospheric pressure during said one phase, and so that the interior of said vessel can be maintained at a pressure below atmospheric pressure during said other phase.

18. The apparatus for processing medical waste materials as defined in claim 12 in which means are provided for adding controlled amounts of steam to the interior of said vessel, such steam causing sterilization of the waste materials to be accomplished.

19. The apparatus for processing medical waste materials as defined in claim 18 in which means are provided for controlling the pressure within said vessel within operational parameters during times of such steam injection.

20. The apparatus for processing medical waste materials as defined in claim 12 in which said drum is inclined at a slight angle to the horizontal, with said inlet end being higher.

21. The apparatus for processing medical waste materials as defined in claim 12 in which said non-obstructive helically configured means is affixed in an unbroken manner along to the interior perimeter of said rotatable drum, for effecting movement of the waste materials within said drum.

22. The apparatus for processing medical waste materials as defined in claim 12 in which said non-obstructive lifting paddles are affixed to the interior perimeter of said rotatable drum to effect movement and agitation of the waste materials within said drum in opposition to the movement of the waste materials by said helically configured means at selected times, and to function in conjunction with the movement of the waste materials by said helically configured means at selected other times.

23. An apparatus for processing medical waste materials comprising an elongate pressure vessel of generally cylindrical configuration having an inlet end, and a closely fitting closure member therefor, said vessel containing an elongate drum of generally cylindrical configuration mounted for rotation about its longitudinal axis, said drum having means for selectively driving it in either rotative direction about such longitudinal axis, said drum having an inlet end corresponding with the inlet end of said vessel, with the longitudinal axis of said drum being at a slight angle of incline to the horizontal, such that the inlet end is at a slightly higher elevation than the opposite end, means for agitating the medical waste within the drum by non-obstructive, helically configured means mounted at spaced locations along the interior perimeter of said drum, such that, during rotation of the drum in a first rotative direction, said helically configured means intercepts the waste materials and tends to move same forward, in the direction away from the inlet end of said drum, whereas during rotation of the drum in the second rotative direction, said helically configured means intercepts the waste materials and tends to move same backward in the direction toward the inlet end of the drum, means for agitating the waste materials within the drum by non-obstructive lifting paddles disposed along the interior perimeter of the drum interspersed between the spacing of said helically configured means, said paddles each being equipped with a plurality of angular surfaces such that during rotation of said drum in the first rotative direction, the first plurality of surfaces of said lifting paddles lift a portion of the waste materials from the mass of waste materials moving through the drum and tend to move such portion of said waste materials backward toward the inlet end of said drum simultaneously with the forward movement of the waste materials as a result of the effect of said helically configured means, with the consequence of a highly advantageous, very thorough mixing of the waste materials being obtained, leading to a very effective contacting of the waste materials with any agent added for accomplishing the sterilization of pathological contaminants, whereas during rotation of the drum in the second rotative direction, said helically configured means intercepts the waste materials and tends to move same backward, in the direction toward the inlet of the drum and simultaneously, with the second plurality of surfaces of said lifting paddles also tending to move the waste materials backward, in the direction toward the inlet of said drum for effecting discharge of the waste materials from the apparatus when the closure member has been opened.

24. The apparatus for processing medical waste materials as defined in claim 23 in which means are provided for adding controlled amounts of moisture to the interior of said vessel, such moisture serving to enhance the penetration of heat into the moisture absorptive materials of the waste materials, thereby enhancing the effort involved in bringing about sterilization.

25. The apparatus for processing medical waste materials as defined in claim 23 in which means are provided for adding controlled amounts of moisture to the interior of said vessel, such moisture serving to increase the density of the moisture absorptive materials of said waste materials so that during the mixing procedure, repulping of the moisture absorptive materials can be accomplished, resulting in a decrease in the volume of the waste materials.

26. The apparatus for processing medical waste materials as defined in claim 23 in which means are provided for adding controlled amounts of heat to the interior of said vessel, such heat serving to soften plastic film containers enclosing the waste materials, causing them to rupture and to gently spill their contents into the interior of the vessel and exposing them to the reactive environment of the interior of the vessel, thereby enhancing the effort involved in bringing about sterilization.

27. The apparatus for processing medical waste materials as defined in claim 23 in which means are provided for adding controlled amounts of steam to the interior of said vessel, such steam causing the plastic containers for the medical waste to become softened, and to spill their contents into the interior of said drum.

28. The apparatus for processing medical waste materials as defined in claim 23 in which said vessel is designed to withstand internal pressure during one phase of the sterilization procedure, and a vacuum condition during another phase of the sterilization procedure, said closure member having means for sealing said inlet end of said vessel so that the interior of said vessel can be maintained at a pressure above atmospheric pressure during said one phase, and so that the interior of said vessel can be maintained at a pressure below atmospheric pressure during said other phase.

29. The apparatus for processing medical waste materials as defined in claim 23 in which means are provided for adding controlled amounts of steam to the interior of said vessel, such steam causing sterilization of the waste materials to be accomplished.

30. The apparatus for processing medical waste materials as defined in claim 24 in which means are provided for controlling the pressure within said vessel within operational parameters during times of such steam injection.

31. The apparatus for processing medical waste materials as defined in claim 23 in which said drum is inclined at a slight angle to the horizontal, with said inlet end being higher.

32. The apparatus for processing medical waste materials as defined in claim 23 in which said non-obstructive helically configured means is affixed in an unbroken manner along to the interior perimeter of said rotatable drum, for effecting movement of the waste materials within said drum.

33. The apparatus for processing medical waste materials as defined in claim 23 in which said non-obstructive lifting paddles are affixed to the interior perimeter of said rotatable drum to effect movement and agitation of the waste materials within said drum in opposition to the movement of the waste materials by said helically configured means at selected times, and to function in conjunction with the movement of the waste materials by said helically configured means at selected other times.

34. A method for processing medical waste materials utilizing a pressure vessel of generally cylindrical configuration, having rotatably mounted in its interior, a drum of generally cylindrical configuration that is mounted to be driven about its longitudinal axis, said pressure vessel having an inlet end and a closure member therefor, said drum having an open inlet adjacent the inlet of said vessel, the interior of said drum being equipped with helically configured means and lifting paddles designed to accomplish complete agitation of the medical waste materials, such method comprising the steps of:
  introducing waste material through the inlet of said vessel, into the inlet of said drum;
  making the vessel pressure tight by closing said closure member;
  driving the drum in rotation about its longitudinal axis, so as to bring about agitation of the waste material in the drum;
  adding heat to the waste material in order to facilitate the sterilization of the waste materials in the drum, and raising the pressure inside the vessel to a level above atmospheric pressure;
  continuing to rotate the drum in the presence of the added heat in order to accomplish considerable agitation and complete contacting of the waste material in the drum with the added heat;
  and thereafter opening said closure member and discharging the treated waste materials from the drum and the vessel.

35. The method as recited in claim 34 in which moisture is added to the waste material in the drum during the rotation of the drum in order to accomplish contacting of moisture absorptive materials in the waste material with the added moisture, to facilitate the penetration of sterilizing heat into the moisture absorptive materials.

36. The method as recited in claim 34 in which large quantities of moisture are added to the waste material in the drum in order to accomplish repulping of the moisture absorptive materials of the waste material such that their volume is reduced.

37. The method as recited in claim 34 in which steam is added to the waste material in the drum during drum rotation, which steam penetrates the waste material to assist in the sterilization procedure.

38. The method as recited in claim 34 in which steam is added to the waste material in the drum during drum rotation, in order to soften plastic containers included in the waste material, causing such plastic containers to rupture and to spill their contents into the interior of the vessel, thus furthering and enhancing sterilization efforts.

39. The method as recited in claim 34 in which sufficient steam is injected during rotation of said drum to bring about an internal temperature of 250° F. and a pressure of 15 psig, in order to accomplish sterilization of the waste materials.

40. The method as recited in claim 34 in which sufficient steam is injected into said vessel during rotation of said drum, to bring about a temperature of 300° F. and a pressure of 50 psig to accomplish sterilization of the waste materials.

* * * * *